United States Patent [19] [11] 4,160,374
Crump et al. [45] Jul. 10, 1979

[54] APPARATUS FOR MEASURING THE DIFFUSIVE RESISTANCE OF PLANT STOMATA

[76] Inventors: Terence J. Crump; Janet M. Crump, both of Carlone House, Church Rd., Ramsden Bellhouse, Billericay, Essex CM11 IRR, England

[21] Appl. No.: 899,600

[22] Filed: Apr. 24, 1978

[51] Int. Cl.² ............................................. G01N 33/00
[52] U.S. Cl. ............................................ 73/76; 73/38
[58] Field of Search ..................... 73/76, 38, 335, 336, 73/73, 432 R

[56] References Cited
U.S. PATENT DOCUMENTS

| 3,463,000 | 8/1969 | Broadwin | 73/76 |
| 3,504,527 | 4/1970 | Marshall | 73/38 |
| 3,688,309 | 8/1972 | Volberg | 73/73 X |
| 3,973,431 | 8/1976 | Ginhoux et al. | 73/76 |

Primary Examiner—Charles A. Ruehl
Assistant Examiner—Joseph W. Roskos
Attorney, Agent, or Firm—Donald D. Jeffery

[57] ABSTRACT

Apparatus for measuring the diffusive resistance of plant stomata includes a cup adapted to be sealingly clamped to a plant leaf being tested to define an enclosed air volume in the cap adjacent the surface of the leaf. A humidity sensor in the cup provides a signal indicative of the humidity of the air in the cup. Control means are provided to receive the output signal from the humidity sensor and are operative to start a counter at a lower set humidity value and to stop the counter at an upper set humidity value thereby to time the rise in humidity between the lower and upper values. Drying means for drying the air within the cup down to a value below the lower set humidity value after each measurement cycle are provided. The control means are adjustable to vary the lower or upper set humidity value and to vary the difference between the lower and upper set humidity values.

7 Claims, 6 Drawing Figures

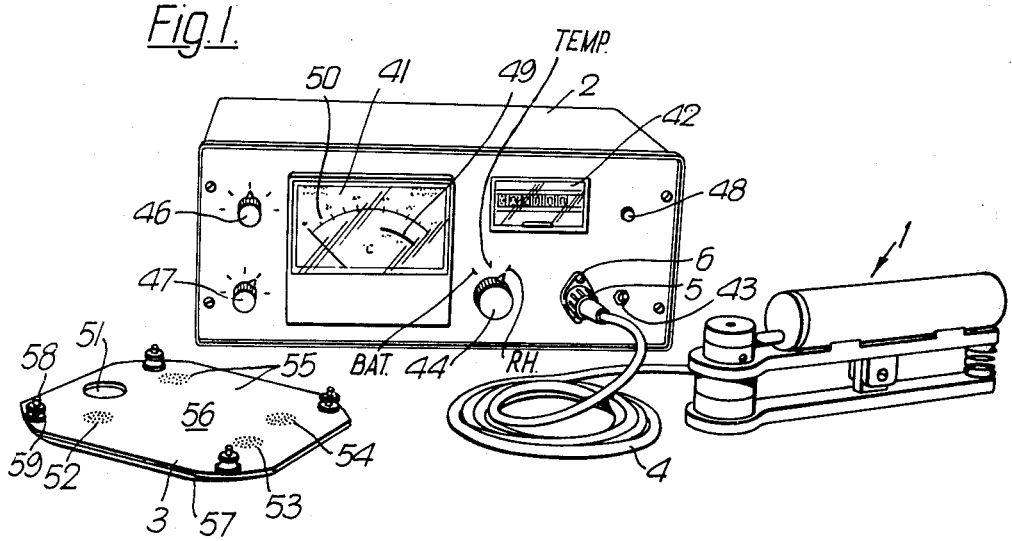
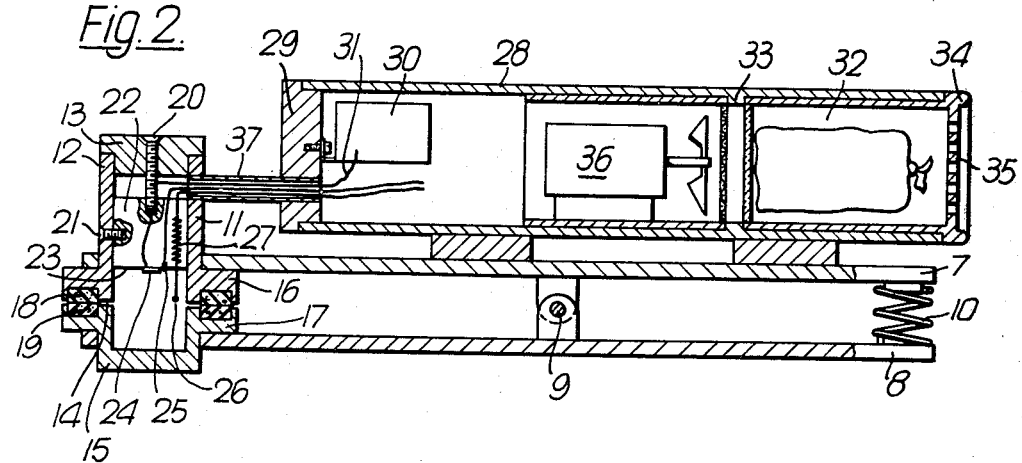

APPARATUS FOR MEASURING THE DIFFUSIVE RESISTANCE OF PLANT STOMATA

BACKGROUND OF THE INVENTION

This invention relates to apparatus for measuring the diffusive resistance of plant stomata.

Measurement of the diffusive resistance of plant stomata is one of the most significant measurements in the determination of water loss by plants. Its measurement is therefore important in the fields of plant science and microclimatology.

The flux of water vapour from a plant leaf is determined by the water vapour concentration gradient between the substomatal cavity and the ambient air and the diffusive resistance in the flow path. The diffusive resistance is the sum of the boundary layer resistance and stomatal resistance.

A known apparatus for measuring diffusive resistance of plant stomata operates by maintaining the boundary layer resistance at a constant value, thus enabling the stomatal resistance to be measured directly. The known apparatus of this kind comprises a cup adapted to be sealingly clamped to a plant leaf being tested to define an enclosed air volume in the cup adjacent to the surface of the leaf. The cup contains a humidity sensor to sense the humidity of the air within the cup and a fan is connected to the cup to enable dry air to be blown into the cup.

The loss of water vapour by the leaf during a measurement cycle increases the humidity of the air within the cup at a rate which depends upon constant characteristics of the cup and upon the diffusive resistance of the leaf. The diffusive resistance is therefore directly related to the rate of increase of humidity of the air within the cup. By measuring the time taken for the humidity to rise between a lower and an upper set value, the value of the diffusive resistance can be found by comparison with an empirical calibration obtained using perforated plates of known diffusive resistance. This measurement is repeated in consecutive measurement cycles, the fan being operated to reduce the humidity of the air within the cup after each measurement cycle in preparation for the next cycle.

In the known apparatus the two set values of humidity are fixed values, for example 60% and 70% relative humidity respectively, and the fan is operated after each measurement cycle to dry the air within the cup down to a humidity lower than the lower set values, i.e. down to a value of 25% relative humidity in the example given. The use of fixed set values of humidity means that the humidity conditions under which the diffusive resistance is measured may differ considerably from the conditions to which the leaf was subjected in the ambient air immediately prior to testing. Moreover, the large repetitive drying range may produce a compensating reaction in the leaf stomata and thus give an erroneous reading.

It is an object of the present invention to provide an improved apparatus which enables the diffusion resistance of plant stomata to be measured more accurately and in conditions which conform more closely to the ambient conditions of the plant before measurement.

SUMMARY OF THE INVENTION

Accordingly, the present invention provides apparatus for measuring the diffusive resistance of plant stomata, including a cup adapted to be sealingly clamped to a plant leaf being tested to define an enclosed air volume in the cup adjacent the surface of the leaf, a humidity sensor in the cup for providing a signal indicative of the humidity of the air in the cup, control means for receiving the output signal from the humidity sensor and operative to start a counter at a lower set humidity value and to stop the counter at an upper set humidity value thereby to time the rise in humidity between the lower and upper values in a measurement cycle, and drying means for drying the air within the cup down to a value below the lower set humidity value after each measurement cycle, in which apparatus the control means is adjustable to vary the lower or upper set humidity value and to vary the difference between the first and second set humidity values.

Preferably, the lower set humidity value is adjustable, for example between 40% and 95% relative humidity (RH) in 5% steps.

Suitable, the difference between the lower and upper set humidity values is adjustable to between 1% and 10% RH in 1% steps.

First and second temperature sensors may be provided in the cup for providing signals indicating the temperatures of the humidity sensor and plant leaf respectively. Advantageously, the control means is connected to receive the output signals of the first and second temperature sensors and is operative to ensure that readings are only taken when the difference between the temperatures of the leaf and humidity sensor do not exceed a predetermined value, for example 0.5° C.

BRIEF DESCRIPTION OF THE DRAWINGS

Further features and advantages of the invention will appear from the following description of a preferred embodiment of the invention, given with reference to the appended drawings, in which:

FIG. 1 is a perspective view of apparatus embodying the invention and comprising a control box, a probe and a calibration plate;

FIG. 2 is a longitudinal sectional view through the probe of the apparatus of FIG. 1;

DESCRIPTION OF PREFERRED EMBODIMENT

Figure 3:
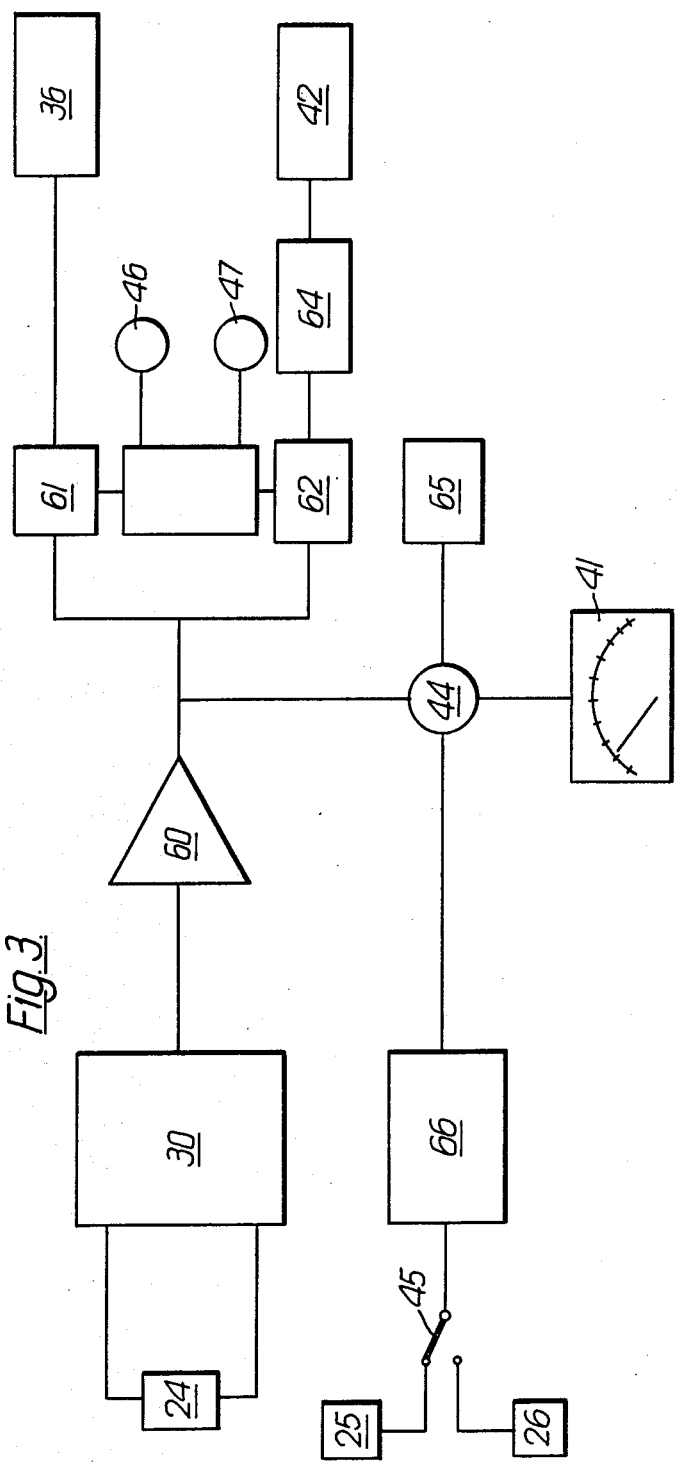
FIG. 3 is a block diagram of electronic circuitry of the apparatus of FIG. 1.

Referring to FIG. 1, a portable apparatus embodying the invention for measuring the diffusive resistance of plant stomata comprises a probe 1, a control box 2 and a calibration plate 3. The probe 1 is electrically connected to the control box 2 by means of a multi-core cable 4 fitted with a multi-pin plug 5 for plugging into a corresponding socket 6 on the control box. The apparatus is adapted to be operated from a battery or from the electrical mains.

As shown in FIG. 2, the probe 1 comprises a clamp in the form of a pair of levers 7 and 8 which are pivotally connected together at 9 intermediate their ends and biased apart at one end by a helical compression spring 10.

At its other end the lever 7 carries an inverted cylindrical cup 11 having an upper end 12 closed by a plug 13 and a lower open end 14 which is closable by a cap 15 carried on the corresponding end of the lever 8. The cup 11 and cap 15 have corresponding channel-shaped annular flanges 16 and 17 each accommodating a respective foam rubber sealing ring 18 or 19.

A screw 20 passing axially through the plug 13 and a screw 21 passing through the cylindrical wall of the cup 11 secures within the cup 11 a cylindrical mounting block 22 which has an end face 23 spaced from the open end 14 of the cup 11 and has five grooves on its cylindrical surface. A humidity sensor 24 is mounted on the end face 23 of the block 22, the sensor 24 being in the form of a thick film capacitor and being, for example, a Vaisala "Humicap" sensor. The sensor 24 provides an electrical signal indicative of the humidity of the air within the cup 11. A first fixed temperature sensor in the form of a first thermistor 25 is carried by the block 22 adjacent the humidity sensor 24 and serves to provide an electrical signal indicative of the temperature of the humidity sensor 24. A second movable temperature sensor in the form of a second thermistor 26 is carried by the block 22 so as to project from the end face 23 of the block 22. The thermistor 26 is spring-loaded by a helical spring 27 so as to press against the surface of a leaf clamped between the cup 11 and cap 15 and provide an electrical signal indicative of the temperature of the leaf.

An aluminium tube 28 is mounted on the upper lever 7 and has one end closed by a plug 29 which also serves for conveniently mounting an oscillator circuit 30 within the tube 28. The oscillator circuit 30 is in the form of a printed circuit sealed in silicone rubber and is connected to humidity sensor 14 by wiring 31. The other end of the tube 28 receives a removable cylindrical cartridge 32 containing silica gel. The cartridge 32 lodges in the end portion of the tube against an internal rib 33 of the tube and has a flanged outer end 34 having a perforated wall 35. An electrical fan 36 is received in the tube 28 adjacent the cartridge 32, a perforated screen 36 being interposed between the fan and cartridge.

The inside of the tube 28 is connected to the inside of cup 11 by a connecting tube 37 which sealingly extends through the plug 29 and the cylindrical wall of cup 11 between the plug 13 and mounting block 22.

The cup 11, cap 15, plugs 13 and 29 and mounting block 22 are made of P.T.F.E. having a low water absorbancy, and the foam rubber of sealing rings 18 and 19 is similarly non-water absorbing.

Referring back to FIG. 1, the control box 2 of the apparatus has a front panel on which are mounted a panel meter 41, a counter 42, an on/off power switch 43, a rotary selector switch 44, a two-way selector switch 45, a first rotary control switch 46, a second rotary control switch 47 and a mains telltale lamp 48.

The rotary selector switch 44 controls the parameter displayed by the panel meter 41 and has: a first position (BAT) in which the meter 41 displays on a first scale 49 the state of a battery of the apparatus; a second position (TEMP) in which the meter 41 displays on a second scale 50 the temperature indicated by thermistor 25 or thermistor 26 depending upon the position of the selector switch 45; and a third position (RH) in which the meter 41 displays on the second scale the relative humidity indicated by the humidity sensor 14.

The first rotary control switch 46 sets a first lower value of the relative humidity at which the counter 42 is started, this lower value being adjustable within a range of 40% to 95% RH in 5% steps. The second rotary control switch 47 sets the difference between the lower set humidity value and an upper humidity value at which the counter 42 is stopped. This difference is adjustable within a range of 1% to 10% RH in 1% steps.

The calibration plate 3 which is shown in FIG. 1 is used to calibrate the apparatus empirically at its various humidity settings. Five circular test areas 51 to 55 corresponding in area to that of the open end of the cup 11 are provided on the plate 3, these test areas being dulled with holes to simulate leaf resistances. The density of holes and the area of the cup determine the level of resistance. One test area 51 comprises an aperture of 2.74 cm$^2$ and the four areas 52-55 are provided respectively with 85,50,27 and 19 holes of 1 mm diameter. The plate 3 comprises an aluminium upper sheet 56 detachably connected to a lower clear acrylic sheet 57 by four bolts 58 and nuts 59. A fine and a coarse layer of filter paper are sandwiched between sheets 56 and 57, the fine filter paper being in contact with the aluminium sheet and the coarse filter paper in contact with the acrylic sheet. Before assembly of the calibration plate, the filter papers are moistened with distilled water and gently pressed to remove any surplus.

FIG. 3 is a block diagram of the elctronic circuitry of the apparatus. The humidity sensor 14 forms half of a capacitance bridge in 1.5 MHZ oscillator 30 so that the output frequency is dependent upon the relative humidity experienced by sensor 14. The output from oscillator 30 is fed to an amplifier 60 which provides a linear output directly related to the relative humidity. The upper and lower set humidity levels are detected by first and second Schmitt triggers 61 and 62 to which the output of amplifier 60 is fed and which are adjustable by the rotary control switches 46 and 47 via humidity level control circuitry. Triggers 61 and 62 control the operation of fan 36 and counter oscillator 64 for counter 42. The selector switch 44 controls the supply of signals to the panel meter 41 from a battery power circuit 65, from the output of amplifier 60 and from a transistorised Wheatstone Bridge circuit 66 connectable to either of thermistors 25 and 26 via two-way switch 45. The circuit 66 may also be connected to disable the counter oscillator if the temperature difference indicated by thermistors 25 and 26 is too great.

Figure 4:
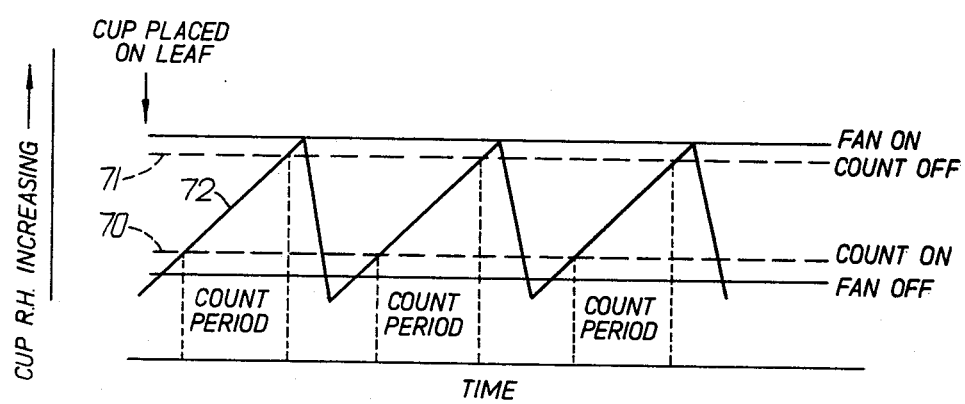
FIG. 4 is a graph of humidity against time, illustrating the operating cycle of the apparatus.

In use of the apparatus, the probe 1 is applied to a plant leaf so that the cup 11 is sealingly applied to the leaf. As shown in FIG. 4 the time for the humidity of the air in the cup 11 to rise between the lower 70 and upper 71 set humidity values is measured in successive automatic measurement cycles. The rising humidity 72 in the cup 11 is monitored by the humidity sensor 14 and the counter 42 is automatically started by the control circuitry when the lower set value 70 is reached and is stopped by the control circuitry when the upper set value 71 is attained.

At the end of each measurement cycle the fan 36 is switched on by the control circuitry to introduce dry air into the cup 11 to dry the cup in readiness for the next measurement. The counter 42 is reset manually. The first and second thermistors 25 and 26 operate to prevent measurements being made if the difference in the temperature of the leaf and humidity sensor 14 exceed 0.5° C.

The count achieved in a measurement cycle can be converted directly into diffusion resistance in sec/cm from a calibration graph produced using the known resistances of the test areas of the calibration plate 3.

Figure 5:
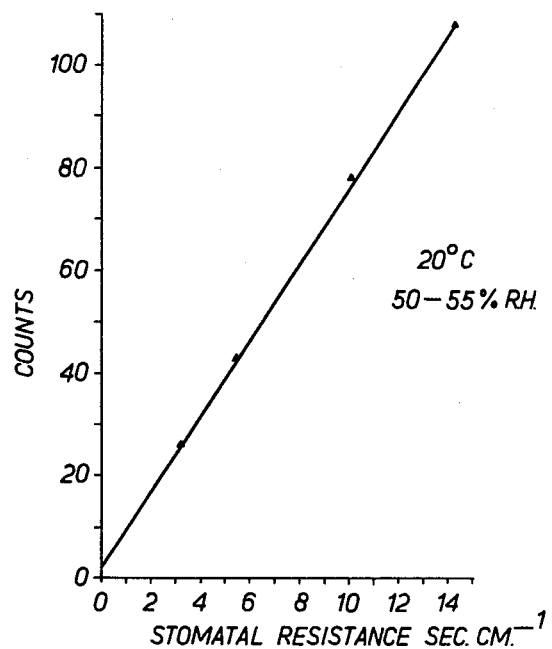
FIG. 5 is a graph showing a calibration curve for particular humidity conditions and temperature.
Figure 6:
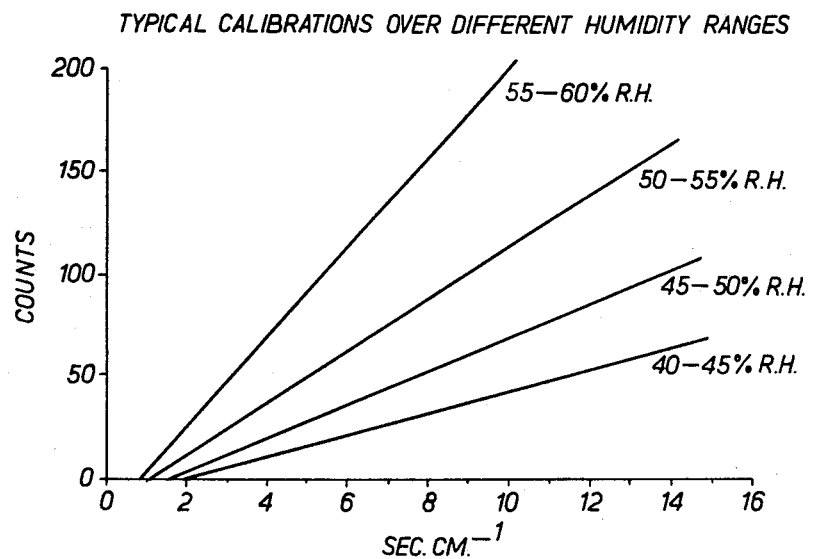
FIG. 6 is a graph showing a number of typical calibration curves for different conditions.

The calibration of the apparatus will vary with the level and difference of the upper and lower set humidity values and with changes in ambient temperature and examples of calibration curves are shown in FIGS. 5 and 6. While it is possible to carry out calibration at the various settings in the laboratory, it is most satisfactory to determine the calibration in the field, at the settings used there. The calibration plate 3 is, in this event, taken into the field in a stiff polythene bag, is kept at a temperature similar to that experienced by the plants being measured and is freed of condensation if necessary before use. Calibration is carried out by clamping the cup 11 over each of the test areas of the calibration plate 3 and obtaining a count for each test area. The counting procedure is repeated several times to obtain a consistent value. Ideally leaf and probe temperature should be the same during calibration and, in any event, the temperature difference should not exceed 0.5° C. A calibration graph as in FIG. 4 can now be plotted. After calibration, observations on leaves can now be made. However, it is recommended that periodic re-calibrations are made, particularly under changing environmental conditions. Any change in the level or difference of the set humidity levels must be followed by re-calibration.

The adjustability of the lower set humidity value and of the difference between the upper and lower set humidity values enables the user of the apparatus to select values which suit his own particular requirements. In particular, the mid-point value between the upper and lower set humidity values can be adjusted to equal the humidity in the ambient air surrounding the plant, to which the plant stomata have adjusted before testing, so that the diffusion resistance values are obtained substantially at the prevailing ambient conditions.

By selecting an appropriately small difference between the upper and lower set humidity and with the fast recycling possible with the apparatus embodying the invention, changes in the stomata diameter during a series of measurement cycles can be minimised thereby enhancing the accuracy of the measurments.

Apparatus embodying the invention may provide measurement of diffusive resistance over a range of from 1 to 15 sec/cm and provide an automatic measurement cycle having a duration of less than 20 seconds at a diffusive resistance of 15 sec/cm.

We claim:
1. Apparatus for measuring the diffusive resistance of plant stomata, comprising:
   a cup;
   means for sealingly clamping said cup to a plant leaf being tested to define an enclosed air volume in said cup adjacent the surface of the leaf; of humidity sensor in said cup for providing a signal indicative of the humidity of the air in said cup;
   a counter;
   control means for receiving the output signal from said humidity sensor and operative to start said counter at a lower set humidity value and to stop said counter at an upper set humidity value, thereby to time the rise in humidity between said lower and upper humidity values in a measurement cycle; and drying means for drying the air within said cup down to a value below said lower set humidity value after each measurement cycle;
   in which apparatus the improvement comprises said control means being adjustable to vary at least one of said lower and upper set humidity values and to vary the difference between said lower and upper set humidity values.

2. Apparatus as claimed in claim 1, wherein said lower set humidity value is variable from 40% to 95% relative humidity.

3. Apparatus as claimed in claim 2, wherein said lower set humidity value is variable in 5% steps.

4. Apparatus as claimed in claim 1, wherein the difference between the lower and upper set humidity values is variable from 1% to 10% relative humidity in 1% steps.

5. Apparatus as claimed in claim 1, comprising first and second temperature sensors in said cup for providing signals indicating the temperatures of said humidity sensor and the plant leaf respectively.

6. Apparatus as claimed in claim 5, wherein said control means is connected to receive the output signals of said first and second temperature sensors and is operative to ensure that readings are only taken when the difference between the temperatures of the leaf and humidity sensor do not exceed a predetermined value.

7. Apparatus as claimed in claim 6, wherein said predetermined value of temperature difference is 0.5° C.

* * * * *